(12) United States Patent
Ahr et al.

(10) Patent No.: US 6,432,097 B1
(45) Date of Patent: Aug. 13, 2002

(54) DISPOSABLE ABSORBENT ARTICLES HAVING TRANSLATIONAL OPERATIVE MEMBERS

(75) Inventors: Nicholas Albert Ahr, Cincinnati; Donald Carroll Roe, West Chester, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/342,298

(22) Filed: Jun. 29, 1999

Related U.S. Application Data

(63) Continuation-in-part of application No. 09/107,563, filed on Jun. 29, 1998, now Pat. No. 6,093,869, and a continuation-in-part of application No. 09/106,225, filed on Jun. 29, 1998, now Pat. No. 6,186,991.
(60) Provisional application No. 60/090,993, filed on Jun. 29, 1998.

(51) Int. Cl.⁷ ................................................. A61F 13/15
(52) U.S. Cl. .................. 604/385.19; 604/361; 604/362; 604/385.16; 604/385.22
(58) Field of Search ................................ 604/361, 362, 604/385.19, 367, 378, 385.01, 385.16, 385.22

(56) References Cited

U.S. PATENT DOCUMENTS

| | | |
|---|---|---|
| 2,681,032 A | 6/1954 | Shaw |
| 3,860,003 A | 1/1975 | Buell |
| 4,418,524 A | 12/1983 | Ito et al. |
| 4,623,342 A | 11/1986 | Ito et al. .................... 604/385 |
| 4,676,785 A | 6/1987 | Battista ...................... 604/369 |
| 4,834,733 A | 5/1989 | Huntoon et al. ............ 604/361 |
| 4,968,312 A | 11/1990 | Khan ........................ 604/388 |
| 5,102,597 A | 4/1992 | Roe et al. |
| 5,124,188 A | 6/1992 | Roe et al. |
| 5,171,236 A | 12/1992 | Dreier et al. |
| 5,330,459 A | 7/1994 | Lavon et al. ............... 604/385 |
| 5,387,207 A | 2/1995 | Dyer et al. |
| 5,428,076 A | 6/1995 | Roe |
| 5,514,121 A | 5/1996 | Roe et al. |
| 5,582,604 A | * 12/1996 | Ahr et al. ................. 604/385.1 |

FOREIGN PATENT DOCUMENTS

| | | | |
|---|---|---|---|
| EP | 0 560 099 | 2/1993 | ............ B01L/3/00 |
| EP | 0 815 821 | 6/1997 | ............ A61F/13/15 |
| FR | 2 485 046 | 12/1981 | ............ D02G/3/24 |
| WO | WO 99/07317 | 2/1999 | ............ A61F/13/15 |

OTHER PUBLICATIONS

"Viscous Fluid Bodily Waste Management Article"–P&G Case 6931 (Ser. #08/970,509), filed on Nov. 14, 1997. Names: Donald C. Roe and Oliver E. C. Mason.

* cited by examiner

Primary Examiner—John G. Weiss
Assistant Examiner—Michael Bogart
(74) Attorney, Agent, or Firm—Jeffrey R. Moore; Jay A. Krebs; Ken K. Patel

(57) ABSTRACT

An absorbent article having a support member comprising a top sheet, a backsheet, or an absorbent core, and a translational operative member for enhancing the capacity for containing bodily waste. The translational operative member is capable of being moved from one region of the article to another or within a region via a translating device. The translating device comprises a moisture sensitive element capable of expanding or contracting when wetted.

36 Claims, 12 Drawing Sheets

DISPOSABLE ABSORBENT ARTICLES HAVING TRANSLATIONAL OPERATIVE MEMBERS

This application is a continuation in part of application Ser. No. 09/107,563 filed Jun. 29, 1998, U.S. Pat. No. 6,093,869 and a continuation in part of application Ser. No. 09/106,225 U.S. Pat. No. 6,186,991 filed Jun. 29, 1998 and claims priority to provisional application Ser. No. 60/090,993 filed Jun. 29, 1998.

FIELD OF THE INVENTION

This invention relates to disposable absorbent articles adapted to be worn by a wearer. More particularly, it relates to disposable absorbent articles having a translational operative member attached to a translating device activated via interaction with exudates discharged from the body of the wearer.

BACKGROUND

The major function of disposable absorbent articles such as diapers and adult incontinence briefs is to prevent bodily waste from soiling, wetting, or otherwise contaminating clothing or other articles, such as bedding, that come in contact with the wearer. In recent years, disposable diapers, such as those disclosed in U.S. Pat. No. 3,860,003 issued to Kenneth Barclay Buell on Jan. 14, 1975, incorporated herein by reference, have become very popular with the public and have generally replaced durable cloth absorbent articles because of their convenience and reliability. However, despite the effectiveness of such disposable absorbent articles, bodily wastes often still leak or are stored in the diaper such that the wastes soil and/or irritate the skin of the wearer. Thus, the search has continued for even more effective devices.

For example, one problem perceived by the caregivers of infants and by the users of, and caregivers of those who wear, adult diapers is that associated with the performance of the disposable diaper which is subjected to multiple discharges of urine (e.g. "insults of urine"). The initial discharge of urine is quickly absorbed by the diaper with no leakage, or run-off, of urine around the sides or ends of the diaper. Subsequent discharges of urine are then absorbed less rapidly than the initial discharge because the absorbent element is already at least partially saturated with urine. In this case, it sometimes occurs that a portion of the second discharge is not absorbed quickly enough to prevent at least a portion of the discharge from leaking around the sides or ends of the diaper.

The undesirable effects of leakage and/or improper containment are especially evident with regard to fecal matter deposited in the diaper. Feces contained in the diaper can harm the skin of the wearer over time and feces leaking from the diaper almost invariably presents unpleasant, messy clean-ups. Several attempts have been made to add features to diapers such as barriers, pockets, spacers, transverse barriers, apertured topsheets and the like to limit the movement of the material across the topsheet and/or to better confine fecal matter in the diaper. However, the success of such attempts has been limited primarily due to containment capacity as well as the ability to reduce the negative effects of the feces.

Accordingly, it would be desirable to provide a disposable absorbent article having increased absorbent and/or containment capacity that would minimize the negative effects of feces or other viscous fluid bodily waste on the wearer or the caregiver. The present invention provides a disposable absorbent articles having translational operative members capable of being moved from one section of the article to another by way of translating devices activated via interaction with initial deposits of bodily waste.

SUMMARY OF THE INVENTION

The present invention is an absorbent article having a primary target zone contiguous with an initial discharge of bodily waste, a support member comprising a top sheet, a backsheet, or an absorbent core, and a translational operative member. The translational operative member can move from one region of the article to another or within a region via a translating device. The translating device, directly or indirectly affixed at one end to the support member and at another end to the translational operative member, comprises a moisture sensitive element capable of expanding or contracting when wetted. The translating device interacts with the primary target zone.

The translational operative member comprises an auxiliary absorbent core, an auxiliary top sheet coated with lotion, a cover for concealing waste, a spacer providing a void for receiving waste, and a pocket for receiving and containing waste. The disposable absorbent article may include any one or combination of operative members.

BRIEF DESCRIPTION OF THE DRAWINGS

These and other features, aspects and advantages of the present invention will become better understood with regard to the following description, appended claims, and accompanying drawings where:

FIG. 12b is a cross-sectional view of the translating device depicted in FIG. 12a.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included drawings.

As used herein, the term "absorbent article" refers to devices which absorb and contain bodily waste, and more specifically, refers to devices which are placed against or in proximity to the body of the wearer to absorb and contain the various exudates discharged from the body. Longitudinal is a direction running parallel to the maximum linear dimension of the article. Longitudinally includes directions within ±45° of the longitudinal direction. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. As used herein, the term "diaper" refers to an absorbent article generally worn by infants and incontinent persons about the lower torso. As used herein "primary target zone" is the point at which bodily waste initiates contact with the disposable absorbent article. Furthermore, when an element is situated, at least in major part, in a position adjacent to the primary target zone, it is said to be in register with the primary target zone. When an element is situated, at least in major part, in a position not adjacent the primary target zone, it is said to be remote from the primary target zone.

Figure 1:
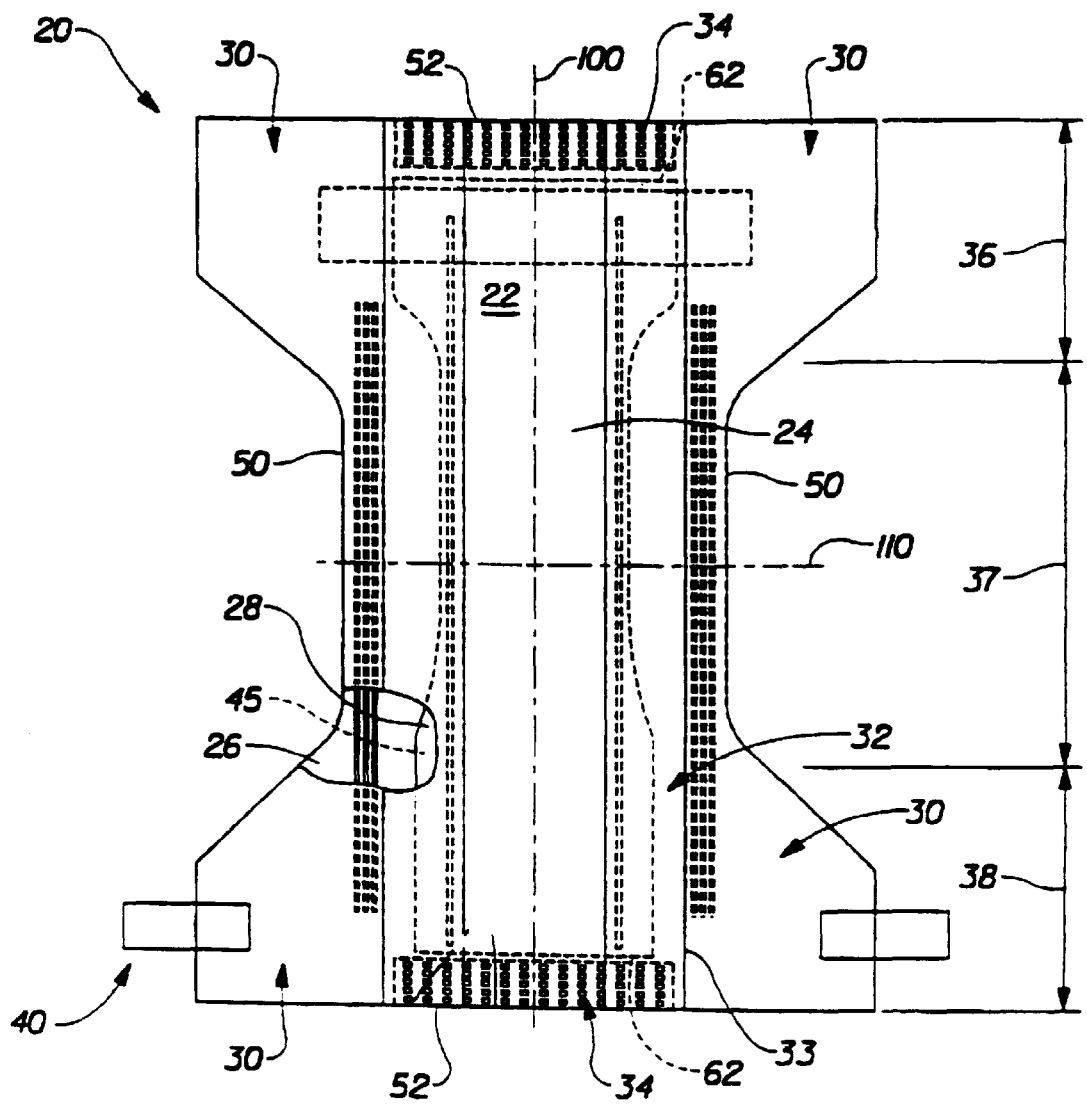
FIG. 1 is a plan view of an absorbent article of the present invention having a portion cut away to reveal the underlying structure, the body-facing surface of the article facing the viewer.

Although the present invention is equally applicable to other absorbent articles such as incontinence briefs, incontinence undergarments, absorbent inserts, diaper holders and liners, feminine hygiene garments, wipes, mops, bandages and the like, a preferred embodiment of an absorbent article of the present invention is the unitary disposable absorbent article, such as diaper 20, shown in FIG. 1.

An embodiment of this invention is an improved disposable diaper. In its simplest embodiment, the disposable diaper of this invention (hereinafter referred to simply as the "diaper"), comprises support members which include a liquid permeable topsheet which, in use, is placed next to the user's body; an impermeable backsheet which, in use, is placed remote from the user's body and adjacent to any outer garment the user should happen to be wearing; a main absorbent core and a translational (i.e. movable) multifunctional operative member referred to herein as an operative member. The operative member may include a pocket for containing waste, a cover providing a barrier for limiting the movement of waste, a spacer providing a void for waste, an auxiliary absorbent core, a waste management element and the like, or any combinations thereof.

The topsheet and the backsheet support members are normally secured to one another about the periphery of the diaper. The main absorbent core support member is interposed between the topsheet and the backsheet and is normally affixed to the backsheet. The operative members are typically situated remote from primary target zones, relative to the support members. However, the operative members may be situated adjacent to the primary target zones depending on the configuration. The operative members are generally not affixed to the support members except as hereinafter described.

The diaper further comprises a translating device for translating (i.e. moving) the operative members relative to the support members. The translating device comprises a moisture sensitive element capable of expanding or contracting when wetted. The moisture sensitive element can be directly or indirectly affixed to the translational operative member.

In certain embodiments, the moisture sensitive element comprises at least one moisture sensitive filament attached at a first point to an operative member. A second point of the moisture sensitive filament, remote from the first point, is attached to one of the support members, such as the main absorbent core, topsheet, or backsheet in such a manner that the filament (i.e., translating device) interacts with a primary target zone. By "interacts with a primary target zone" it is meant that the translating device is in register with the primary target zone and, thereby, directly wetted by the initial flow of bodily waste as it contacts the primary target zone or, alternatively, is remote from the primary target zone and is wetted indirectly by, for example, fluid transport from the primary target zone to the translating device. When the filament is wetted, it shrinks and generally draws the operative member into register with the primary target zone, so that the benefits achieved by moving the operative member can be realized such as providing additional waste containment, concealing waste, and/or providing a relatively fresh region in place to receive subsequent discharges of waste. In general, the translating device functions to provide a movement or change of position of the operative member relative to the remainder of the article and/or the wearer.

Figure 12A:
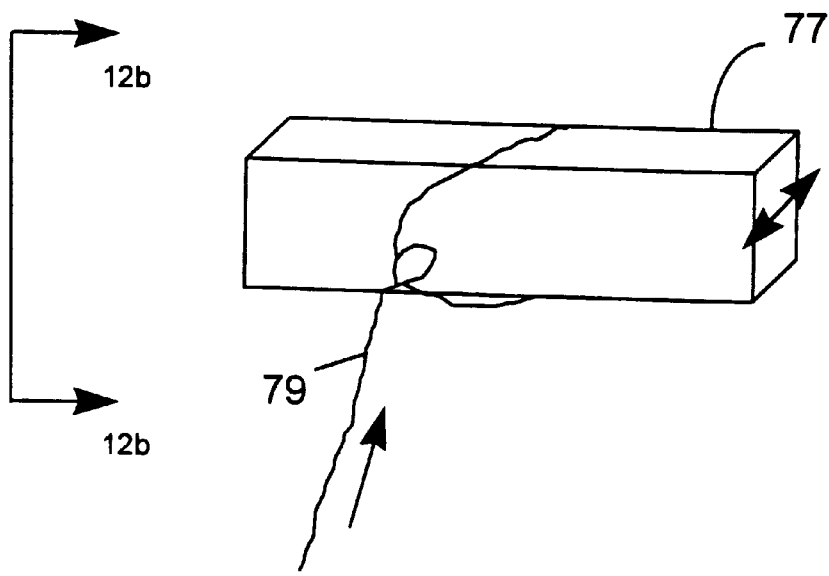
FIG. 12a is a view of a translating device embodiment of the present invention comprising a connecting element looped to an expandable element.
Figure 12B:
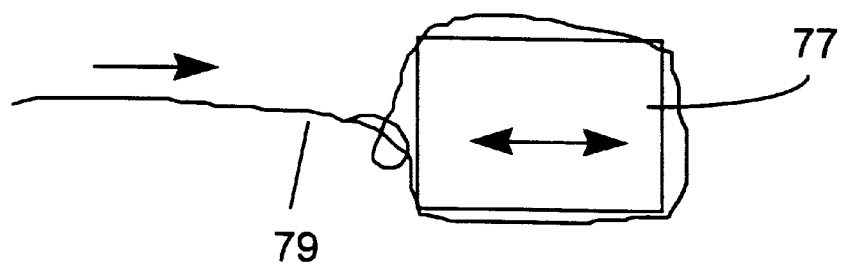

In alternative embodiments, illustrated in FIGS. 12a and 12b, the translating device may comprise an expandable element 77 that directly, or indirectly, translates the operative member 70 relative to at least a portion of the article or the wearer. The expandable element 77 may, for example, comprise an expandable foam or porous absorbent polymeric macrostructure which expand when contacted by water. Suitable expandable foams are thin-until-wet high internal phase emulsion foams as described in U.S. Pat. No. 5,387,207 entitled "Thin-Until-Wet Absorbent Foam Materials For Aqueous Body Fluids And Process For Making Same" issued to Dyer et al. on Feb. 7, 1995 incorporated herein by reference. Suitable expandable porous absorbent polymeric macrostructures are described in more detail in U.S. Pat. No. 5,102,597 issued to Roe et al. Apr. 7, 1992;

U.S. Pat. No. 5,124,188 issued to Roe et al. Jun. 23, 1992 and U.S. Pat. No. 5,428,076 issued to Roe Jun. 27, 1995 all of which are incorporated herein by reference. The expandable element 77 may be connected directly to the operative member 70 or may be indirectly connected via a connecting element 79 such as a string (shrinkable or non-shrinkable), scrim, film, tape, or any other suitable means. In some embodiments, as shown in FIG. 12a and 12b, the connecting element 79 is wrapped around the expandable element 77 in its non-expanded state in a loop or "noose" type arrangement, such that when the expandable element expands, the connecting element 79 will translate the operative member 70 a distance equivalent to the increase in circumscribed perimeter of the expandable element 77.

Regardless of the exact nature or structure of the translating device, it may be activated (i.e., caused to shrink, expand, rotate, change morphology, or any other action that results in translation of the operative member) by any energizer as known in the art, including moisture (i.e., water), temperature (e.g., certain NIPAM gels as known in the art expand or contract with a temperature change), a change in pH, and electric fields (e.g., as in the case of electrically sensitive gels as known in the art).

FIG. 1 is a plan view of the diaper 20 of the present invention in a flat-out, state with portions of the structure being cut-away to more clearly show the support members of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 1 to have a first waist region 36, a second waist region 38 opposed to the first waist region 36 and a crotch region 37 located between the first waist region and the second waist region. The periphery of the diaper 20 is defined by outer edges of the diaper 20 in which longitudinal edges 50 run generally parallel to a longitudinal centerline 100 of the diaper 20 and end edges 52 run between the longitudinal edges 50 generally parallel to a lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core 28. In such cases, the holder and/or the liner may include a fastening element which is used to hold the liner in place throughout the time of use.) For unitary absorbent articles, the chassis 22 comprises the main structure of the diaper 20 with other features added to form the composite diaper structure. While the topsheet 24, the backsheet 26, and the absorbent core 28 may be assembled in a variety of well known configurations, typical diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/723,179 entitled "Absorbent Article With Multi-Directional Extensible Side Panels" filed Sep. 30, 1996 in the name of Robles et al.; each of which is incorporated herein by reference.

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, IN and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, OH under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body surface of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheet 24 includes fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet 24 more rapidly. This diminishes the likelihood that bodily waste will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet 24. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein. Alternatively, the topsheet 24 may include an apertured web or film which is hydrophobic. This may be accomplished eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. Nos. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet 24 may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet 24 or backsheet 26 may be embossed and/or matte finished to provide a more cloth like appearance.

The absorbent core 28 may comprise any absorbent material which is generallycompressible, conformable, non-irritating to the wearer's skin, and capable of absorbing and retaining liquids such as urine and other certain bodily waste. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to Des Marais et al. on Jul. 22, 1997. Each of these patents is incorporated herein by reference.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably maintains the first waist region 36 and the second waist region 38 in an overlapping configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. Each of these patents is incorporated herein by reference. In alternative embodiments, opposing sides of the garment may be seamed or welded to form a pant. This allows the article to be used as a pull-on type diaper, such as a training pant.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaper pulls one elasticized side panel 30 farther than the other during application, the diaper 20 will "self-adjust" during wear.

While the diaper 20 of the present invention typically has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

The diaper 20 may further include leg cuffs 32 which provide improved containment of liquids and other bodily waste. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

Embodiments of the present invention may also include a waste management element capable of effectively and efficiently accepting, storing and/or immobilizing viscous fluid bodily waste, such as runny feces. The waste management element can be located anywhere in the article, including the crotch region or either waist region, or may be associated with or be included in any support member or element such as the core 28, a leg cuff, etc. In preferred embodiments, the waste management element is located in the region of the article that is near the wearer's perianal region when worn. This helps ensure that any waste discharged is deposited on or near the waste management element. Examples of waste management elements for use in absorbent products are described in copending application Ser. No. 08/970509, filed Nov. 14, 1997, allowed Feb. 19, 1999 entitled "Viscous Fluid Bodily Waste Management Article".

Figure 2:
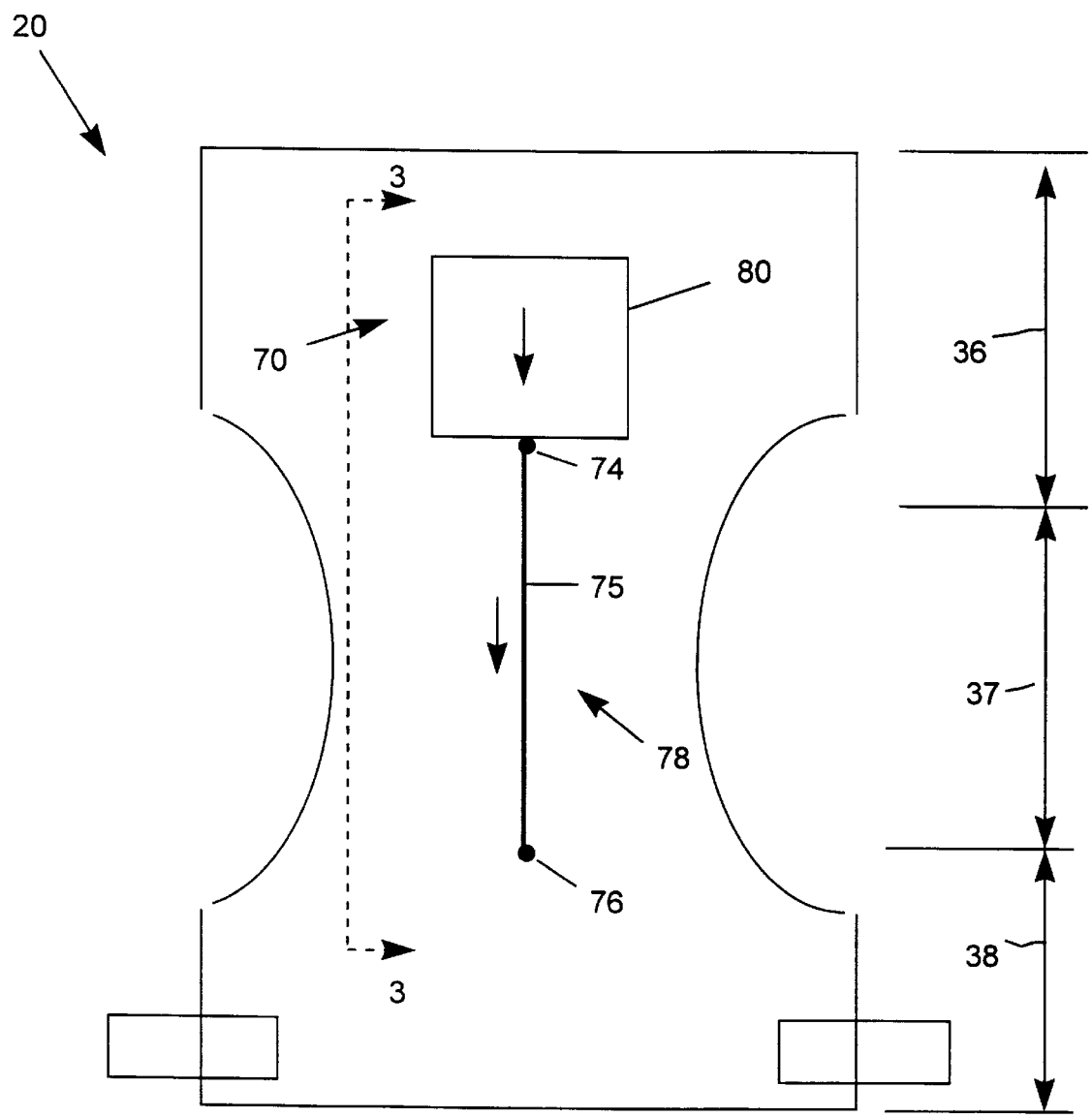
FIG. 2 is a plan view of an absorbent article embodiment of the present invention wherein the operative member comprises an auxiliary absorbent core.

FIG. 2 is a plan view of diaper 20 of FIG. 1 from which topsheet 24 has been removed so that the internal arrangement of elements can be more readily observed. Diaper 20 comprises backsheet 26, main absorbent core 28, operative member 70, and a translating device 78 comprising a moisture sensitive element. For the embodiment shown in FIG. 2, the operative member 70 comprises an auxiliary absorbent core 80 and the moisture sensitive element comprises a moisture sensitive filament 75. The auxiliary absorbent core 80 is movable (e.g. "translational") with respect to main absorbent core 28 via the filament 75.

The filament 75 is affixed to the auxiliary absorbent core 80 at first attachment point 74 and to main absorbent core 28 at second attachment point 76. The filament 75 may be attached to the first and second attachment points 74, 76 by any convenient means, such as by the use of common hot melt adhesive.

The moisture sensitive element, shown in FIG. 2 is a single filament 75, however, it is to be understood that multiple filaments can be used at the discretion of the manufacturer. Further, a tape or other similar elongate structure can be used in place of the filament 75.

The moisture sensitive filament 75 includes materials which shrink (i.e. which become shorter) when they are wetted with water, urine, or other fluid bodily waste. The moisture sensitive filament 75 can be elastic before shrinking, after shrinking, or both before and after shrinking, but elasticity is not a necessary property for use in the present invention. Exemplary moisture sensitive filaments are discussed in detail in U.S. Pat. No. 4,418,524 issued to Ito et al on Dec. 6, 1983, which patent is incorporated herein by reference. The degree of shrinkage of any moisture sensitive filament used in the practice of this invention should be suitable for translating the operative member to a location desired depending on the configuration.

For example, the moisture sensitive filament 75 may comprise a composite of at least one moisture sensitive filament comprising carboxymethylated cellulose having a degree of substitution of from about 0.15 to about 0.4 and at least one ordinary (e.g. non-moisture sensitive) filament to, among other attributes, enhance the overall strength of the composite. In another embodiment, the composite may comprise one moisture sensitive filament and one ordinary filament. The composite may be twisted to enhance its moisture sensitive attributes. The moisture sensitive filament will shrink from about 50% to about 75%, preferably to about 90%, of its original length when wetted with urine, or other fluid bodily waste.

Figure 4:
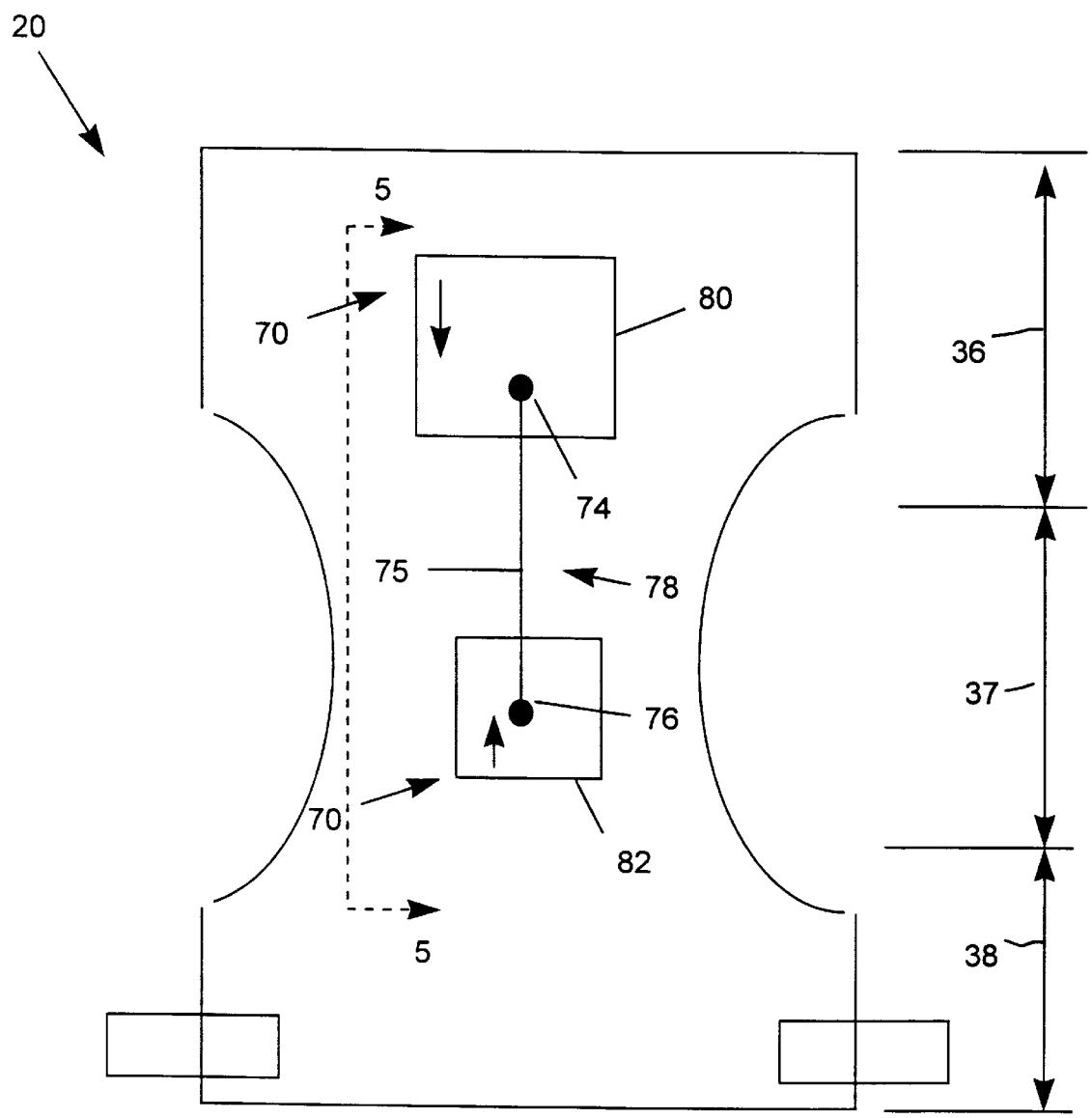
FIG. 4 is a plan view of an absorbent article embodiment of the present invention wherein the operative member comprises two auxiliary absorbent cores connected via a translating device.
Figure 5:
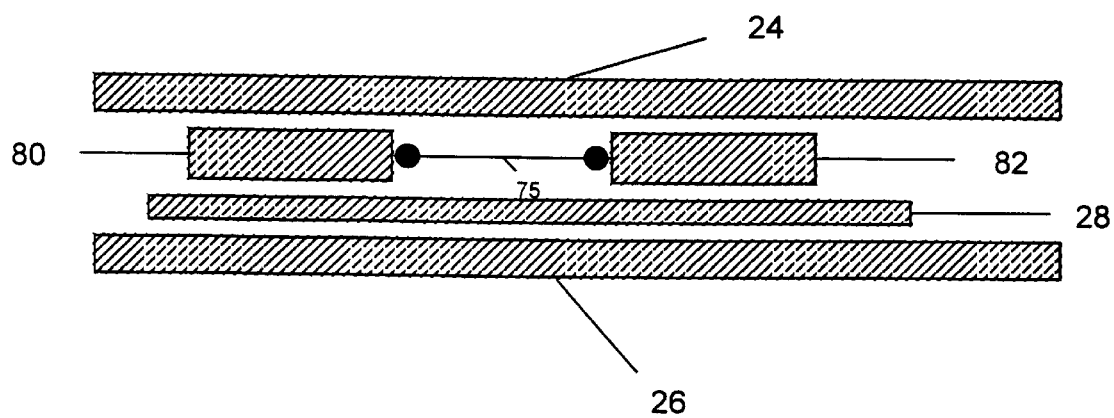
FIG. 5 is a cross sectional view of the absorbent article of FIG. 4 depicting the two auxiliary absorbent cores connected via a translating device.

In an alternate embodiment shown in FIGS. 4 and 5, the Diaper 20 comprises backsheet 26, main absorbent core 28, and two operative members comprising auxiliary absorbent core 80 and a second auxiliary absorbent core 82 connected via moisture sensitive filament 75. Moisture sensitive filament 75 is affixed to auxiliary absorbent core 80 at first attachment point 74 and to the second auxiliary absorbent core 82 at second attachment point 76. Auxiliary absorbent core 80 and second auxiliary absorbent core 82 are movable (e.g. "translational") with respect to main absorbent core 28 and with respect to each other. In use, moisture causes the filament 75 to contract thereby drawing auxiliary absorbent cores 80 and 82 together and into the target zone.

Figure 3:
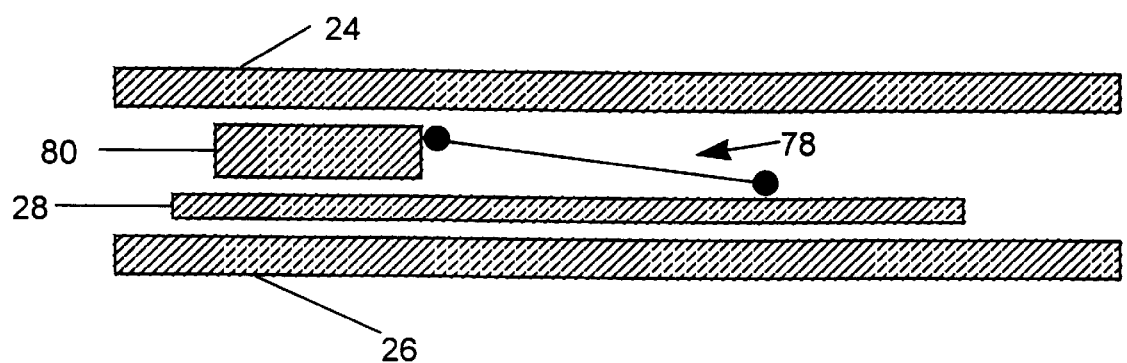
FIG. 3 is a cross sectional view of the absorbent article of FIG. 2 depicting the auxiliary absorbent core and the translating device.

The distinction between diaper 20 of FIGS. 2 and 3 and diaper 20 of FIGS. 4 and 5 is that the diaper configuration shown in FIGS. 4 and 5 comprises two movable auxiliary absorbent cores 80 and 82 while diaper configuration shown in FIGS. 2 and 3 comprises only a single movable auxiliary absorbent core 80. The materials and methods of construction of the two diaper configurations are similar and the discussions above apply equally to both configurations.

In FIGS. 4 and 5, moisture sensitive filament 75 is shown attached to auxiliary absorbent cores 80 and 82. In other versions of this invention, not illustrated, multiple moisture sensitive filaments can be used (as described above) and each of such multiple moisture sensitive filaments can be attached between the multiple auxiliary absorbent cores or between one of the auxiliary absorbent cores and the main absorbent core 28.

Figure 6:
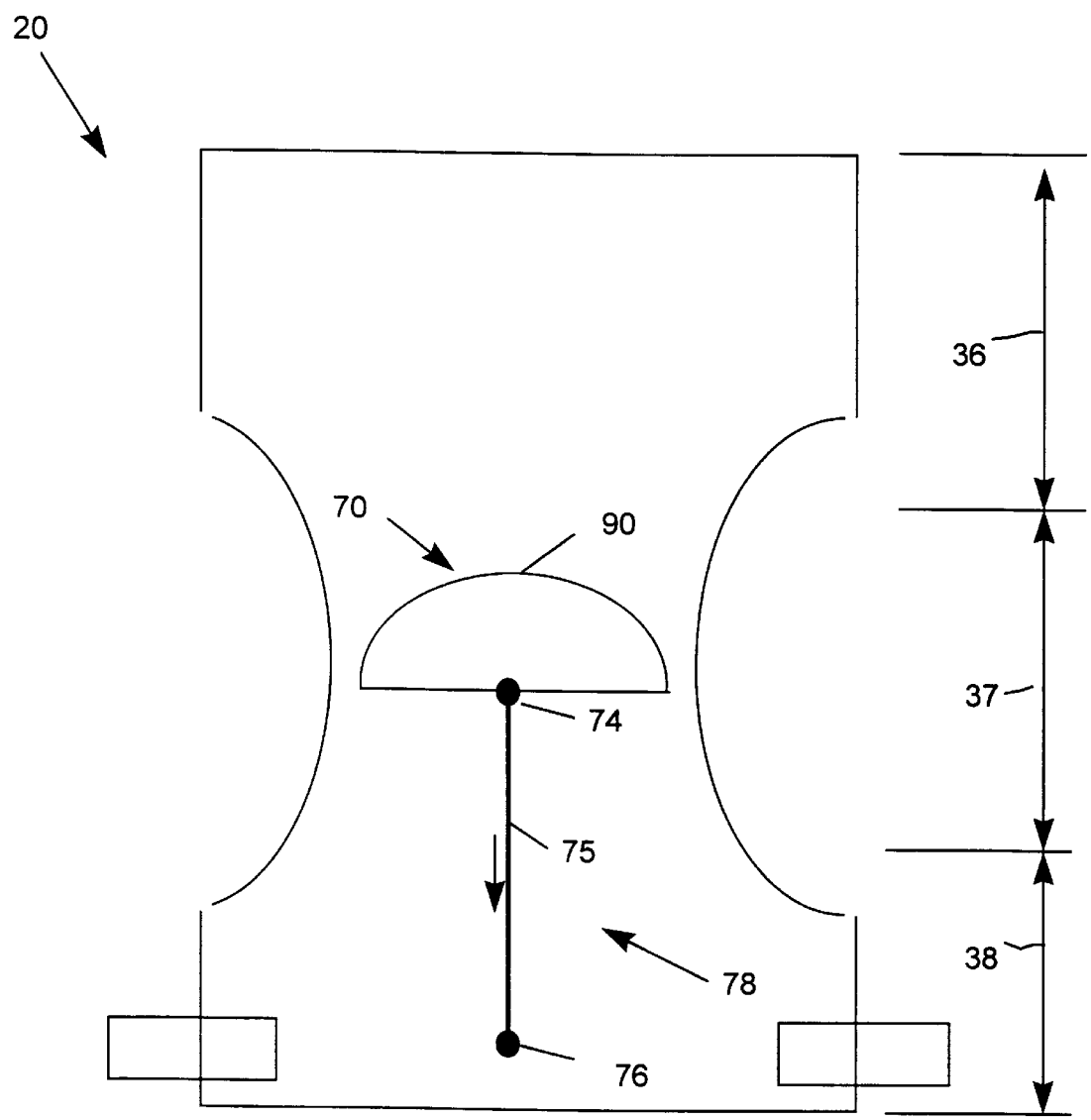
FIG. 6 is a plan view of an absorbent article embodiment of the present invention wherein the operative member comprises a pocket for containing waste.
Figure 7:
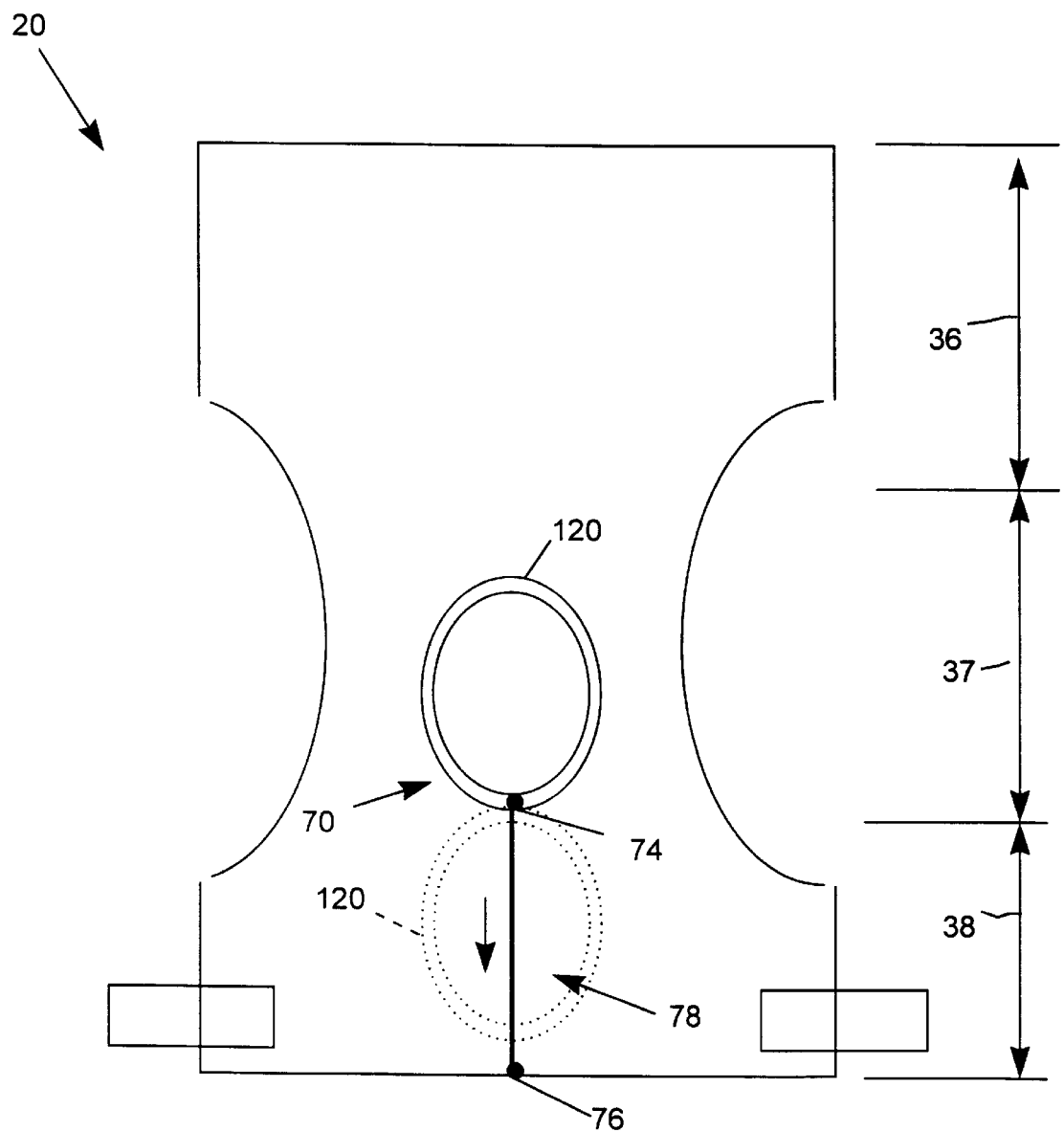
FIG. 7 is a plan view of an absorbent article embodiment of the present invention wherein the operative member comprises a spacer providing a void for waste.
Figure 8:
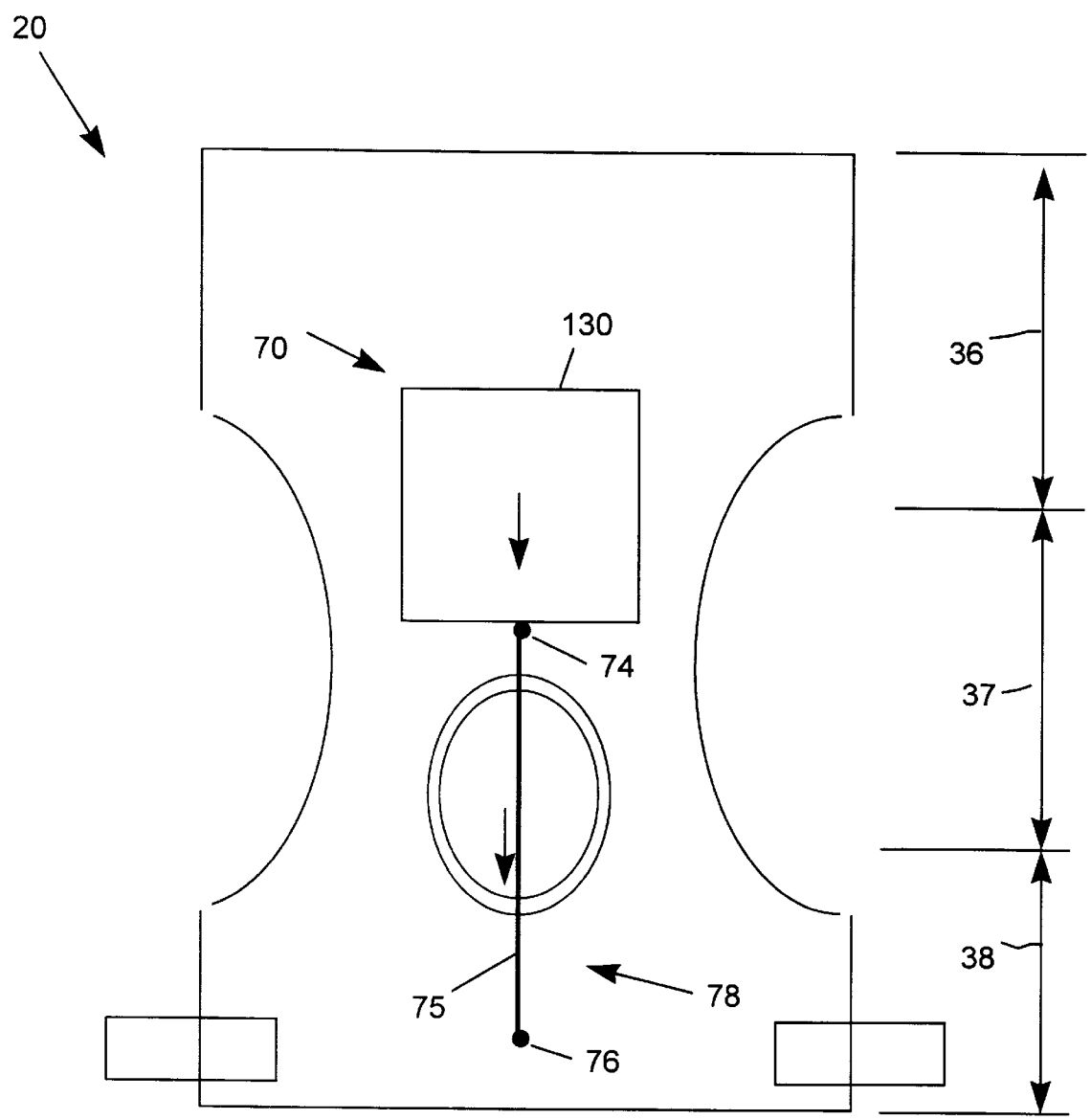
FIG. 8 is plan view of an absorbent article embodiment of the present invention wherein the operative member comprises a cover providing a barrier for limiting the movement of waste.
Figure 9:
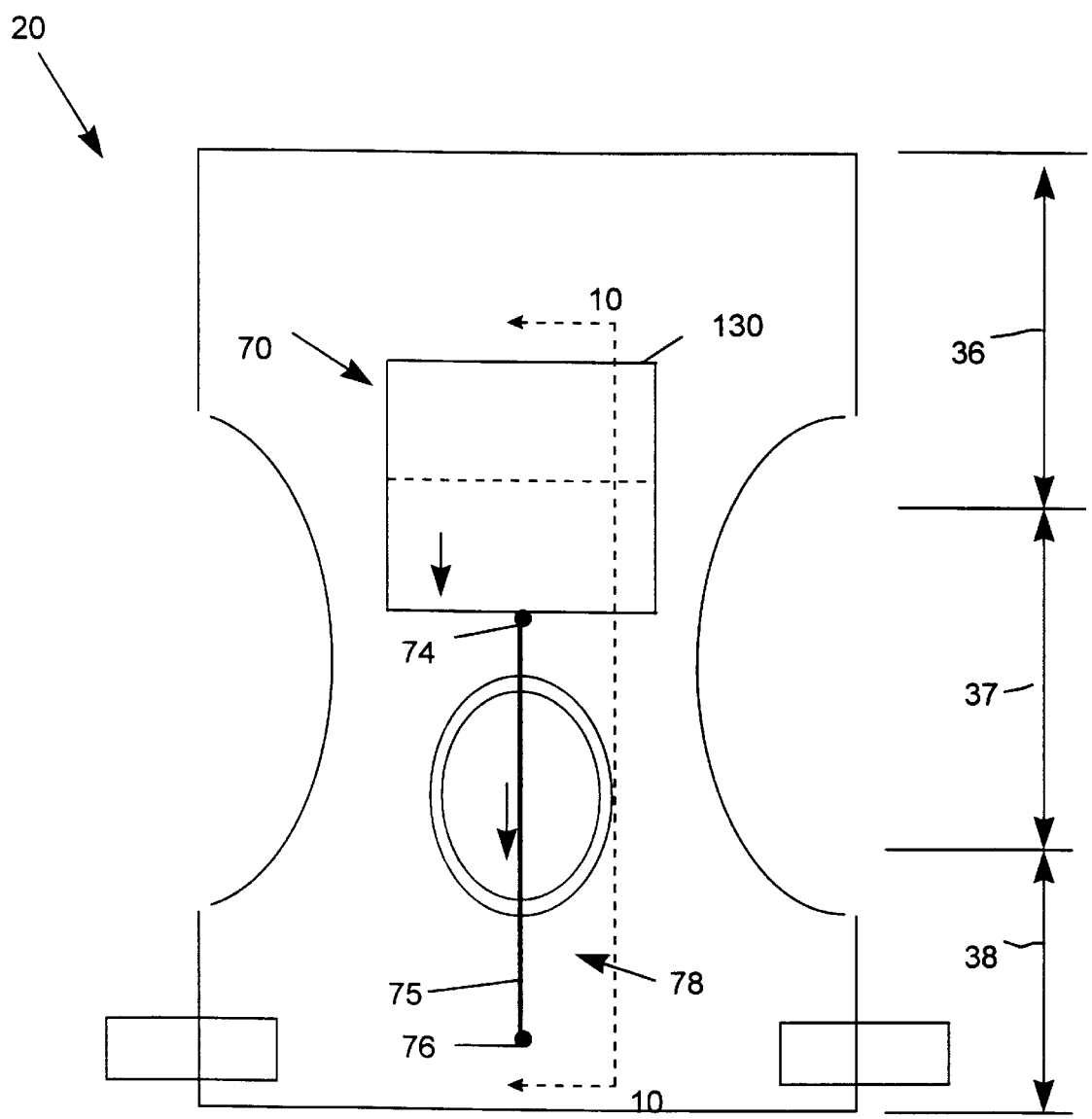
FIG. 9 is a plan view of an absorbent article embodiment illustrated in FIG. 8 wherein the cover is a part of the topsheet.
Figure 10:
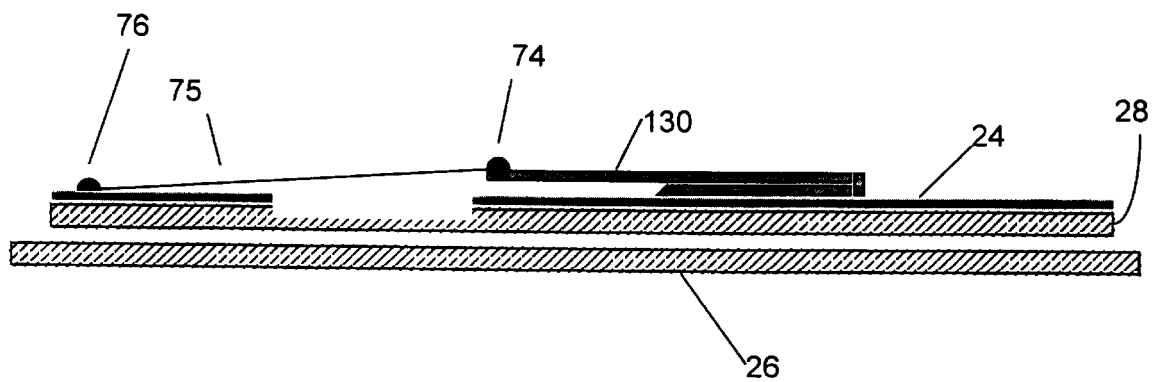
FIG. 10 is a cross-sectional view of the embodiment shown in FIG. 9 depicting the cover as a folded portion of the top sheet.
Figure 11:
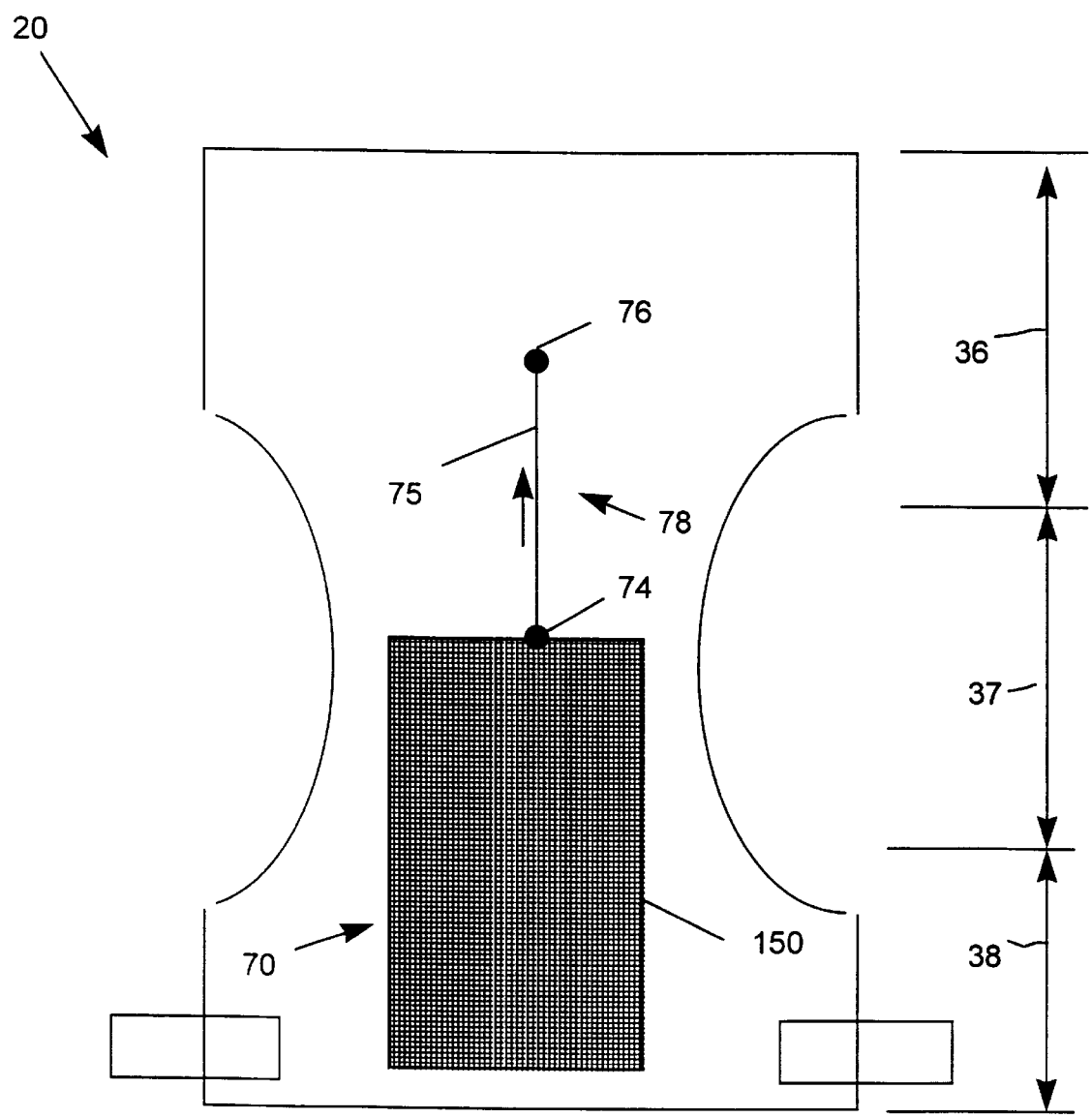
FIG. 11 is a plan view of an absorbent article embodiment of the present invention wherein the operative member comprises a waste management element.

Other embodiments of the present invention include such translational operative members 70 as previously described including a pocket 90 for containing waste illustrated in FIG. 6; a spacer 120 providing a void for waste illustrated in FIG. 7; a cover 130 providing a barrier for limiting the movement of waste illustrated in FIG. 8, 9 and 10; an auxiliary top sheet coated with lotion for applying lotion to the skin of a wearer; and a waste management element 150 illustrated in FIG. 11 or combinations thereof.

A pocket 90 for containing waste is described in U.S. Pat. No. 5,514,121 issued to Roe et al. on May 7, 1996. The pocket 90, illustrated in FIG. 6, collects and receives fecal material, thereby preventing it from excessively spreading and smearing against the skin of the wearer. The pocket 90 may be oriented longitudinally concave towards the first waist region, longitudinally concave toward the second waste region 38, may be a closed figure, or may simply present a straight barrier. As a translational operative member, the pocket can be made to move longitudinally relative to the support members via the translating device 78 physically scooping the fecal material in order to enhance the pocket's effectiveness in collecting and receiving the bodily waste.

In another embodiment, the translational operative member comprises a spacer 120 providing a void space for feces. The spacer 120, illustrated in FIG. 7, keeps the void space open while the weight of the wearer's body is imposed on the topsheet 24. The spacer 120 is generally a linear element having a longitudinal dimension substantially greater than any other dimension and are generally longitudinally oriented. The spacer 120 can be made of rubber or foam material with open cell foam being preferred over closed cell foams in order to minimize occurrences of red marking. Once activated, the translating device 78 may move the spacer 120 into a position that conceals the waste from the wearer's skin and/or provides space for additional fecal discharges.

In another embodiment, the operative member may include a cover 130 providing a barrier for limiting the movement of waste. The cover 130 illustrated in FIG. 8, can be used in conjunction with the spacer 130 providing a void space. Once the wearer defecates, the cover 130 can be made to slide over the void space via the translating device 78, concealing the fecal material from the wearer's skin. As shown in FIGS. 9 and 10, the cover 130 can include a separate sheet or a folded portion of the topsheet 24.

Another embodiment for the operative member which may serve as a cover 130 and is similar in operation to the cover 130 is an auxiliary topsheet 24 coated with lotion. The lotion coated topsheet 24 is disposed remote from the primary target zone between the topsheet 24 and the wearer's skin. Once activated, the translating device slides the lotion coated topsheet 24 between the article and the wearer's skin, thereby transferring the lotion to the wearer's skin.

In another embodiment, the operative member may comprise a waste management element 150. As previously described, the waste management element 150, illustrated in FIG. 11, is preferably located in the crotch region of the article that is near the wearer's perianal region when worn. Generally, due to gravitational effects, fecal material collected within the element tends to settle in the crotch region 37 mid-way between the first waist region 36 and the second waist region 38, thus, minimizing the effective area utilized by the waste management element 150. By making the waste management element 150 an operative member 70 that can be translated longitudinally, the effective area of the element 150 is enhanced.

For each of the embodiments previously described, the first attachment point 74 of the translating device 78 is affixed to the operative member 70 while the second attachment point 76 is affixed to a support member such as the top sheet 24, the backsheet 26, or the absorbent core 28. For each embodiment, the translating device 78 interacts with the primary target zone which can be the point at which the fecal material or urine initiates contact with the top sheet 24.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An absorbent article having a first waist region, a second waist region opposed to the first waist region, a crotch region disposed between the first waist region and the second waist region and a primary target zone, the absorbent article comprising:
   a support member;
   an absorbent core;
   a translational operative member juxtaposed the support member; and
   a translating device comprising a moisture sensitive element capable of expanding or contracting when wetted, having a first end joined to the translational operative member and a second end joined to the support member such that a portion of the translating device interacts with the primary target zone expanding or contracting when wetted and causing the translational operating member to move relative to the support member.

2. The absorbent article of claim 1 wherein the support member includes one of the following: a top sheet, a backsheet, or an absorbent core.

3. The absorbent article of claim 1 wherein the moisture sensitive element comprises a filament composed of carboxymethylated cellulose having a degree of substitution of from about 0.15 to about 0.4.

4. The absorbent article of claim 3 wherein the filament will shrink from about 50% to about 75% of its original length when wetted.

5. The absorbent article of claim 3 wherein the filament will shrink about 90% of its original length when wetted.

6. The absorbent article of claim 1 wherein the moisture sensitive element comprises an expandable element.

7. The absorbent article of claim 6 wherein the translating device further comprises a connecting element joining the operative member to the expandable element.

8. The absorbent article of claim 7 wherein connecting element includes one or more of the following: a string, a scrim, a film, a tape, and a nonwoven.

9. The absorbent article of claim 1, wherein the translating device is activated by one or more of the following energizers: moisture, heat, change in pH, and an electric field.

10. The absorbent article of claim 1 wherein the operative member comprises a pocket for receiving and containing waste such that as the pocket is moved by the translating device, the waste is scooped into the pocket.

11. The absorbent article of claim 1 wherein the operative member comprises a spacer providing a void for receiving waste such that as the spacer is moved by the translating device the waste contained therein is concealed from a wearer's skin providing additional space for subsequent waste.

12. The absorbent article of claim 2 wherein the operative member comprises a cover such that as the cover is moved by the translating device, the cover conceals waste from the wearer's skin.

13. The absorbent article of claim 12 wherein the cover comprises a portion of the top sheet.

14. The absorbent article of claim 2 wherein the operative member comprises an auxiliary lotion coated top sheet such that as the lotion coated top sheet is moved by the translating device the lotion is transferred to the wearer's skin.

15. The absorbent article of claim 1 wherein the operative member comprises an auxiliary absorbent core that is moved into a position by the translating device to provide additional absorption capacity for bodily waste.

16. The absorbent article of claim 1 wherein the operative member comprises a waste management element having an effective area which is enhanced as the waste management element is moved by the translating device.

17. A sanitary napkin having a first region, a second region opposed to the first region, a crotch region disposed between the first region and the second region, and a primary target zone, the absorbent article comprising:
    a backsheet joined with topsheet;
    an absorbent core disposed between at least a portion of the topsheet and the backsheet;
    a translational operative member juxtaposed the topsheet; and
    a translating device comprising a moisture sensitive element capable of expanding or contracting when wetted, having a first end joined to the translational operative member and a second end joined to the topsheet such that a portion of the translating device interacts with the primary target zone such that the translational operative member may be moved relative to the topsheet by the translating device.

18. The absorbent article of claim 17 wherein the operative member comprises a cover that conceals exudates from the wearer's skin as the cover is moved by the translating device.

19. The absorbent article of claim 17 wherein the cover comprises a portion of the top sheet.

20. The absorbent article of claim 17 wherein the operative member comprises an auxiliary lotion coated top sheet such that as the lotion coated top sheet is moved by the translating device lotion is transferred to the wearer's skin.

21. The absorbent article of claim 17 wherein the operative member comprises an auxiliary absorbent core that can be moved into a position by the translating device to provide additional absorption capacity for exudates.

22. An absorbent article having a first waist region, a second waist region opposed to the first waist region, a crotch region disposed between the first waist region and the second waist region, and at least one primary target zone, the absorbent article comprising:
    a backsheet joined with the topsheet;
    an absorbent core disposed between at least a portion of the topsheet and the backsheet;
    a plurality of translational operative members juxtaposed the topsheet; and
    a plurality of translating devices comprising a moisture sensitive element capable of expanding or contracting when wetted, having first ends joined to the translational operative members and second ends joined to the topsheet such that portions of the translating devices interact with the at least one primary target zone such that the translational operative members may be moved relative to the topsheet by the translating devices.

23. The absorbent article of claim 22 wherein the moisture sensitive element comprises a filament composed of carboxymethylated cellulose having a degree of substitution of from about 0.15 to about 0.4.

24. The absorbent article of claim 23 wherein the filament will shrink from about 50% to about 75% of its original length when wetted.

25. The absorbent article of claim 23 wherein the filament will shrink about 90% of its original length when wetted.

26. The absorbent article of claim 22 wherein the moisture sensitive element comprises an expandable element.

27. The absorbent article of claim 26 wherein the translating device further comprises a connecting element joining the operative member to the expandable element.

28. The absorbent article of claim 27 wherein connecting element includes one or more of the following: a string, a scrim, a film, a tape, or a nonwoven.

29. The absorbent article of claim 22, wherein the plurality of translating devices are activated by one or more of the following energizers: moisture, heat, change in pH, or electric field.

30. The absorbent article of claim 22 wherein the plurality of operative members includes a pocket for receiving and containing waste such that as the pocket is moved by the translating device, the waste is scooped into the pocket.

31. The absorbent article of claim 22 wherein the plurality of operative members includes a spacer providing a void for receiving waste such that as the spacer is moved by the translating device the waste contained therein is concealed from a wearer's skin providing additional space for subsequent waste.

32. The absorbent article of claim 22 wherein the plurality of operative members includes a cover such that as the cover is moved by the translating device it conceals waste from the wearer's skin.

33. The absorbent article of claim 32 wherein the cover comprises a portion of the top sheet.

34. The absorbent article of claim 22 wherein the plurality of operative members includes an auxiliary lotion coated top sheet such that as the lotion coated top sheet is moved by the translating device lotion is transferred to the wearer's skin.

35. The absorbent article of claim 22 wherein the plurality of operative members includes an auxiliary absorbent core that can be moved into a position by the translating device providing additional absorption capacity for bodily waste.

36. The absorbent article of claim 22 wherein the plurality of operative members includes a waste management element having an effective area which is enhanced as the waste management element is moved by the translating device.

* * * * *